United States Patent
Khanzhin et al.

(10) Patent No.: US 8,420,667 B2
(45) Date of Patent: *Apr. 16, 2013

(54) ISOQUINOLINONE DERIVATIVES AS NK3 ANTAGONISTS

(75) Inventors: Nikolay Khanzhin, Humlebaek (DK); Karsten Juhl, Greve (DK); Soren Moller Nielsen, Hillerod (DK); Klaus Baek Simonsen, Odense (DK)

(73) Assignee: H. Lundbeck A/S, Valby (DK)

( * ) Notice: Subject to any disclaimer, the term of this patent is extended or adjusted under 35 U.S.C. 154(b) by 171 days.

This patent is subject to a terminal disclaimer.

(21) Appl. No.: 12/988,631

(22) PCT Filed: Apr. 22, 2009

(86) PCT No.: PCT/EP2009/054806
§ 371 (c)(1),
(2), (4) Date: Jan. 4, 2011

(87) PCT Pub. No.: WO2009/130240
PCT Pub. Date: Oct. 29, 2009

(65) Prior Publication Data
US 2011/0130420 A1 Jun. 2, 2011

(30) Foreign Application Priority Data
Apr. 24, 2008 (WO) ................ PCT/DK2008/050092

(51) Int. Cl.
*C07D 217/24* (2006.01)
*A61K 31/472* (2006.01)

(52) U.S. Cl.
USPC .......................................... 514/309; 546/141

(58) Field of Classification Search .................. None
See application file for complete search history.

(56) References Cited

U.S. PATENT DOCUMENTS

| 8,173,639 B2 * | 5/2012 | Simonsen et al. ............ 514/218 |
| 2009/0143402 A1 | 6/2009 | Simonsen et al. |
| 2010/0076016 A1 | 3/2010 | Khanzhin et al. |

FOREIGN PATENT DOCUMENTS

| WO | WO 95/32948 | 12/1995 |
| WO | WO 2005/014575 | 2/2005 |
| WO | WO 2006/050991 | 5/2006 |
| WO | WO 2006/050992 | 5/2006 |
| WO | WO 2006/130080 | 12/2006 |
| WO | WO 2008/131779 | 11/2008 |
| WO | 2009/156339 A1 | 12/2009 |
| WO | 2010/028655 A1 | 3/2010 |

OTHER PUBLICATIONS

Jeffrey and Potts, "Neurokinin-3 receptor antagonists in schizophrenia" Expert Opinion on Therapeutic Patents, 2006, 16, 925-937.
Spooren, et al., "NK3 receptor antagonists: the next generation of antipsychotics?" Nature Reviews, 2005, 4, 967-975.
Meltzer, et al., "Placebo-Controlled Evaluation of Four Novel Compounds for the Treatment of Schizophrenia and Schizoaffective Disorder" Am. J. Psychiatry, 2004.161.975-984.
Evangelista, "Talnetant" Curr.Opion.Invest.Drug, 2005, 6, 717-721.
Modi and Usgaonkar, "Isoquinolines: Part IV—Synthesis of 3-Methyl, 3-Formyl & Other 3-Substituted N-Aryllsoquinolones" Ind. J.Chem., 1979, 18B, 304-306.
Langlois, et al., "Use of the B-Imager for Rapid ex Vivo Autoradiography Exemplified with Central Nervous System Penetrating . . . " J.Pharm.Exp.Ther., 2001, 299, 712-717.
Yip and Chaul., "Localization of Fos-like immunoreactivity induced by NK3 tachykinin receptor agonist, senktide, in the guinea-pig brain" Br. J. Phar., 1997, 122, 715-722.
Fioramonti, et al., "Intestinal anti-nociceptive behaviour of NK3 receptor antagonism in conscious rats: evidence to . . . " Neurogastroenterol. Motil., 2003, 15, 363-369.
Mazelin, et al., "Comparative effects of nonpeptide tachykinin receptor antagonists on experimental gut inflammation in rats and guinea pigs" Life Sci., 1998, 63, 293-304.
Daoui, et al., "Involvement of Tachykinin NK3 Receptors in Citric Acid-induced Cough and Bronchial Responses in Guinea Pigs" Am. J. Respir. Crit. Care Med., 1998, 158, 42-48.
Maubach, et al., "Tachykinins may modify spontaneous epileptiform activity in the rat entorhinal cortex in vitro by activating gabaergic . . . " Neurosci., 1998, 83, 1047-1062.
Kemel, et al., "Facilitation by Endogenous Tachykinins of the NDMA-Evoked Release of Acetylcholine after Acute and Chronic Suppression of . . . " J. Neurosci., 2002, 22, 1929-1936.
Dai, et al., "Efficient Rhodium-Catalyzed Asymmetric Hydrogenation for the Synthesis of a New Class of N-Aryl beta-Amino Acid Derivatives" Org. Lett., 2005, 7, 5343-5345.
Liu, et al., "Synthesis of Enantiomerically Pure N-tert-Butanesulfinyl Imines (tert-Butanesulfinimines) by the Direct Condensation . . . " J. Org. Chem., 1999, 64, 1278-1284.
Cogan, et al., "Asymetric Synthesis of Chiral Amines by Highly Diastereoselective 1,2-Additions of Organometallic Reagents to . . . " Tetrahedron, 1999, 55, 8883-8904.

(Continued)

*Primary Examiner* — Zinna Northington Davis
(74) *Attorney, Agent, or Firm* — Stephen G. Kalinchak; Mary Catherine Di Nunzio; Kitae Lim

(57) ABSTRACT

Isoquinolone derivatives of the general formula Ik" are provided. The compounds are NK3 antagonists and useful for the treatment of e.g. psychosis and schizophrenia.

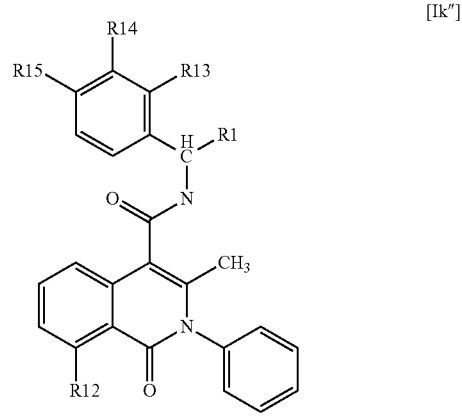

[Ik"]

14 Claims, No Drawings

OTHER PUBLICATIONS

Amato, et al., "Synthesis of 1-tert-Butyl-4-chloropiperidine: Generation of an N-tert-Butyl Group by the Reaction of a Dimethyliminium . . . " J. Org. Chem., 2005, 70, 1930-1933.

Glossop, A Microwave-Assisted Alternative Synthesis of 8-Amino-2-methyl-3,4-dihydroisoquinolin-1-one, Synthesis, 2007, 7, 981-983.

Sugaya, et al., "Synthesis of a 6H-Pyrazolo[4,5,1-de]acridin-6-one Derivative: A useful Intermediate of anti-tumour Agents" Synthesis, 1994, 1, 73-76.

Albert "Neurokinin antagonists and their potential role in treating depression and other stress disorders" Expert Opin. Ther. Patents, 2004, 14, 1421-1433.

Berge, et al., "Pharmaceutical Salts" Journal of Pharmaceutical Sciences, 66:1, 1-19. 1977.

Giardina, Guiseppe A. M. et al., 1997, Discovery of a Novel Class Selective Non-Peptide Antagonists for the Human Neurokinin-3 Reeceptor. 1. Identification of the 4-Quinolinecarboxamide Framework, Journal of Medicinal Chemistry, vol. (40) No. 12, p. 1794-1807.

Giardina, G.A.M. et al., 1999, Replacement of the quinoline system in 2-phenyl-4-quinolinecarboxamide NK-3 receptor antagonists, Il Farmaco, 54, 365-374.

* cited by examiner

ISOQUINOLINONE DERIVATIVES AS NK3 ANTAGONISTS

CROSS-REFERENCE TO RELATED APPLICATIONS

The present application is a U.S. National Stage Application of International Application No. PCT/EP2009/054806, filed Apr. 22, 2009 and claims the benefit of International Application No. PCT/DK2008/050092, filed Apr. 24, 2008 both of which are incorporated by reference herein.

FIELD OF THE INVENTION

The present invention relates to compounds useful in therapy, in particular in the treatment of psychosis, to compositions comprising said compounds, and to methods of treating diseases comprising the administration of said compounds.

BACKGROUND OF THE INVENTION

The currently approved antipsychotic drugs share the common feature of reducing the dopamine signalling in the brain. This is achieved through either a dopamine D2 receptor antagonistic or partial agonistic effect. The first generation antipsychotics (also referred to as "typical") are often associated with extra-pyramidal side effects wherefore the use of these agents have diminished. Second generation or "atypical" antipsychotics in addition to the D2 receptor affinity have affinity to the serotonin receptor 2A ($5\text{-}HT_{2A}$). Some atypical antipsychotics in addition have affinity for the $5\text{-}HT_{2C}$, $5\text{-}HT_6$, or $5\text{-}HT_7$ receptors. Atypical antipsychotics give rise to fewer extra-pyrimidal side effects, but are still hampered by weight gain and $QT_C$ effects. Examples of atypicals are clozapine, olanzapine and risperidone.

More recently, neurokinin receptors have been suggested as targets for CNS diseases [Albert, *Expert Opin. Ther. Patents*, 14, 1421-1433, 2004]. Neurokinins (or tachykinins) are a family of neuropeptides, which include substance P (SP), neurokinin A (NKA), and neurokinin B (NKB). The biological effects of these substances are primarily effected through binding to and activation of the three neurokinin receptors NK1, NK2, and NK3. Although some cross reactivity probably exists, SP has the highest affinity and is believed to be the endogenous ligand for NK1, and likewise for NKA and NK2, and for NKB and NK3.

NK3 is primarily expressed centrally in regions including cortical regions, such as frontal, parietal and cingulated cortex; nuclei of the amygdala, such as the basal, central and lateral nuclei; the hippocampus; and mesencephalon structures, such as ventral tegmental area, substantia nigra pars compacta, and dorsal raphe nuclei [Spooren et al, *Nature Reviews*, 4, 967-975, 2005]. The NK3 receptor is expressed on dopaminergic neurons, and Spooren et al has suggested that the antipsychotic effects of NK3 antagonists are mediated by an inhibition of the dopamine tone, particularly at the D2 receptor combined with a reduction of the serotonergic tone, particularly at the $5\text{-}HT_{2A}$ receptor.

Two structurally distinct NK3 antagonists, namely talnetant and osanetant, have been clinically tested for antipsychotic, and in particular antischizophrenic effects.

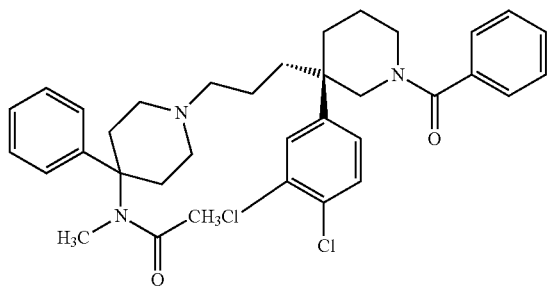

Osanetant

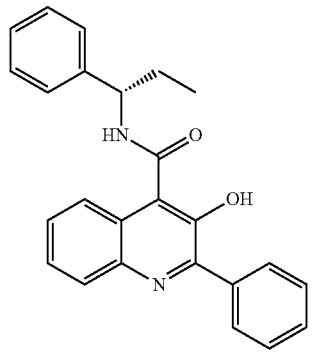

Talnetant

Osanetant proved superior to placebo in clinical trials, in particular on positive symptoms of psychosis, i.e. delusions, hallucinations and paranoia [*Am. J. Psychiatry*, 161, 2004, 975-984]. Similarly, talnetant has been shown in clinical trials to ameliorate the cognitive behaviour of schizophrenics [*Curr. Opion. Invest. Drug*, 6, 717-721, 2005]. Nevertheless, both compounds are hampered by poor pharmacokinetic and pharmacodynamic properties including poor solubility, poor bioavailability, relatively high clearance, and poor blood-brain barrier penetration [*Nature reviews*, 4, 967-975, 2005]. These results lend support to the notion that the NK3 receptor is a promising target for the treatment of e.g. psychosis, however emphasising the need for identifying compounds with adequate pharmacokinetic and pharmacodynamic properties.

WO95/32948 discloses a range of quinoline derivatives, including talnetant as NK3 antagonists.

More recently, WO 2006/130080 discloses compounds having the core structure

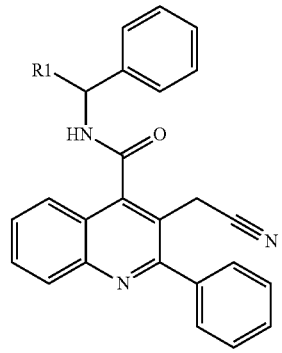

which compounds are said to be NK3 antagonists; and WO 2006/050991 and WO 2006/050992 disclose further quinolinecarboxamides derivatives, which derivatives are said to be NK3 antagonists.

WO 2005/014575 discloses compounds of the formula

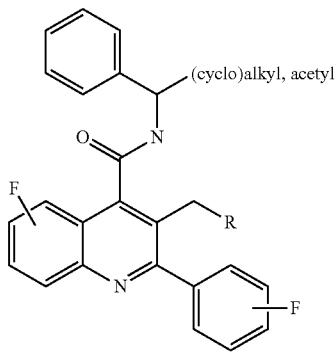

wherein R represents N-containing heterocycles, i.e. pyrazolyl, triazolyl and tetrazolyl.

WO 2008/131779 discloses that isoquinolone derivatives of the formula

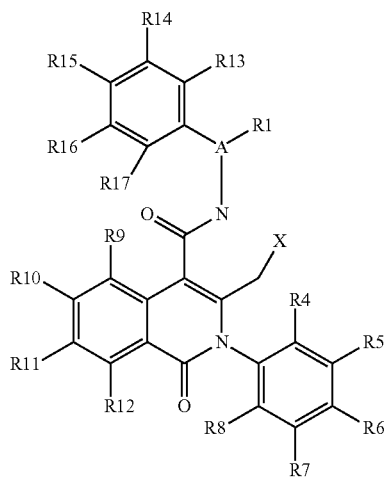

are NK3 antagonists.

Finally, *Ind. J. Chem. Section B*, 18B, 304-306, 1979 discloses a study on the synthesis of compounds with the following core structure

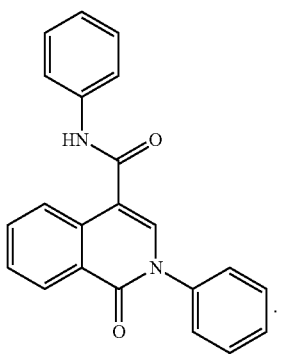 [SMILES: O=C(Nc1ccccc1)c1cn(-c2ccccc2)c(=O)c2ccccc12]

SUMMARY OF THE INVENTION

The present inventors have surprisingly found that certain isoquinolinone derivatives are potent NK3 antagonists, which may as such be used in the treatment of e.g. psychosis. Accordingly, in one embodiment the invention relates to compounds of formula Ik"

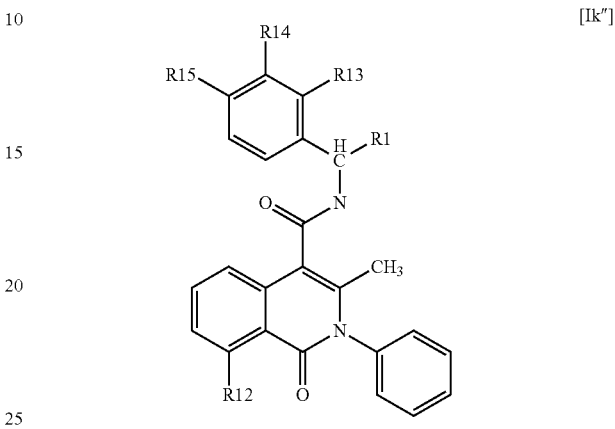

[Ik"]

wherein $R^1$ represents ethyl, cyclopropyl or cyclobutyl;
wherein $R^{12}$ represents fluoro or chloro; and
$R^{13}$, $R^{14}$ and $R^{15}$ each individually represent hydrogen, fluoro or chloro, wherein two of $R^{13}$, $R^{14}$ and $R^{15}$ represent hydrogen;
and pharmaceutically acceptable salts thereof.

In one embodiment, the invention relates to compounds of formula Ik" and pharmaceutically acceptable salts thereof for use in therapy.

In one embodiment, the invention relates to pharmaceutical compositions comprising compounds of formula Ik" and pharmaceutically acceptable salts thereof.

In one embodiment, the invention relates to methods of treatment, which methods comprise the administration of therapeutically effective amounts of a compound of formula Ik" and pharmaceutically acceptable salts thereof to a patient in need thereof.

In one embodiment, the invention relates to the use of a compound of formula Ik" and pharmaceutically acceptable salts thereof in the manufacture of a medicament.

In one embodiment, the invention relates to compounds of formula Ik" and pharmaceutically acceptable salts thereof for use in the treatment of diseases.

DEFINITIONS

In the present context, pharmaceutically acceptable salts include pharmaceutical acceptable acid addition salts, pharmaceutically acceptable metal salts, ammonium and alkylated ammonium salts. Acid addition salts include salts of inorganic acids as well as organic acids.

Examples of suitable inorganic acids include hydrochloric, hydrobromic, hydroiodic, phosphoric, sulfuric, sulfamic, nitric acids and the like.

Examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutical acceptable inorganic or organic acid addition salts include the pharmaceutically acceptable salts listed in J. Pharm. Sci. 1977, 66, 2, which is incorporated herein by reference.

Examples of metal salts include lithium, sodium, potassium, magnesium salts and the like.

Examples of ammonium and alkylated ammonium salts include ammonium, methyl-, dimethyl-, trimethyl-, ethyl-, hydroxyethyl-, diethyl-, n-butyl-, sec-butyl-, tert-butyl-, tetramethylammonium salts and the like.

In the present context, the term "therapeutically effective amount" of a compound means an amount sufficient to cure, alleviate or partially arrest the clinical manifestations of a given disease and its complications in a therapeutic intervention comprising the administration of said compound. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

In the present context, the term "treatment" and "treating" means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. Nonetheless, prophylactic (preventive) and therapeutic (curative) treatments are two separate aspects of the invention. The patient to be treated is preferably a mammal, in particular a human being.

DETAILED DESCRIPTION OF THE INVENTION

In one embodiment, the compounds of the invention are defined by formula Ik''

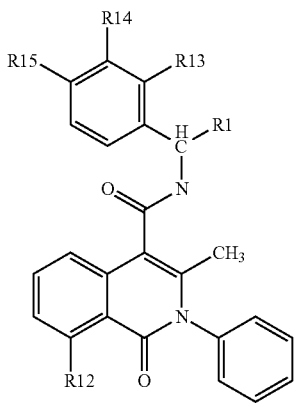

[Ik'']

wherein $R^1$ represents ethyl, cyclopropyl or cyclobutyl;
wherein $R^{12}$ represents fluoro or chloro; and $R^{13}$, $R^{14}$ and $R^{15}$ each individually represent hydrogen, fluoro or chloro, wherein two of $R^{13}$, $R^{14}$ and $R^{15}$ represent hydrogen,
and pharmaceutically acceptable salts thereof. In particular, said compound is essentially the S enantiomers as depicted in formula Ik'''

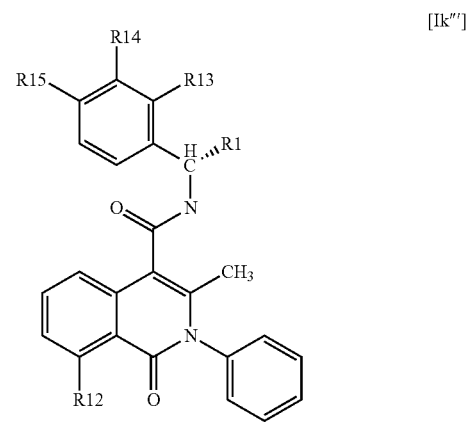

[Ik''']

wherein $R^1$ represents ethyl or cyclopropyl;
wherein $R^{12}$ represents fluoro or chloro; and $R^{13}$, $R^{14}$ and $R^{15}$ each individually represent hydrogen, fluoro or chloro, wherein two of $R^{13}$, $R^{14}$ and $R^{15}$ represent hydrogen.

In one embodiment the compounds of the present invention are selected from the below list.

1as 8-Chloro-3-methyl-1-oxo-2-phenyl-1,2-dihydro-isoquinoline-4-carboxylic acid [(S)-1-(4-chloro-phenyl)-propyl]-amide 1at 8-Chloro-3-methyl-1-oxo-2-phenyl-1,2-dihydro-isoquinoline-4-carboxylic acid [(S)-1-(4-fluoro-phenyl)-propyl]-amide 1au 8-Chloro-3-methyl-1-oxo-2-phenyl-1,2-dihydro-isoquinoline-4-carboxylic acid [(S)-1-(2-fluoro-phenyl)-propyl]-amide 1av 8-Chloro-3-methyl-1-oxo-2-phenyl-1,2-dihydro-isoquinoline-4-carboxylic acid [(S)-1-(3-chloro-phenyl)-propyl]-amide 1aw 8-Chloro-3-methyl-1-oxo-2-phenyl-1,2-dihydro-isoquinoline-4-carboxylic acid [(S)-(3-chloro-phenyl)-cyclopropyl-methyl]-amide 1ax 8-Chloro-3-methyl-1-oxo-2-phenyl-1,2-dihydro-isoquinoline-4-carboxylic acid [(S)-(4-chloro-phenyl)-cyclopropyl-methyl]-amide 1ay 8-Chloro-3-methyl-1-oxo-2-phenyl-1,2-dihydro-isoquinoline-4-carboxylic acid [(S)-1-(3-fluoro-phenyl)-propyl]-amide 1ba 8-Chloro-3-methyl-1-oxo-2-phenyl-1,2-dihydro-isoquinoline-4-carboxylic acid [(S)-cyclopropyl-(4-fluorophenyl)-methyl]-amide 1bb 8-Chloro-3-methyl-1-oxo-2-phenyl-1,2-dihydro-isoquinoline-4-carboxylic acid [(S)-1-(2-chloro-phenyl)-propyl]-amide 1bd 8-Chloro-3-methyl-1-oxo-2-phenyl-1,2-dihydro-isoquinoline-4-carboxylic acid [(S)-(2-chloro-phenyl)-cyclopropyl-methyl]-amide 1be 8-Chloro-3-methyl-1-oxo-2-phenyl-1,2-dihydro-isoquinoline-4-carboxylic acid [(S)-cyclopropyl-(2-fluorophenyl)-methyl]-amide 1bh 8-Chloro-3-methyl-1-oxo-2-phenyl-1,2-dihydro-isoquinoline-4-carboxylic acid [(S)-cyclobutyl-(3-fluorophenyl)-methyl]-amide 1bi 8-Chloro-3-methyl-1-oxo-2-phenyl-1,2-dihydro-isoquinoline-4-carboxylic acid [(S)-cyclobutyl-(4-fluorophenyl)-methyl]-amide 1bl 8-Chloro-3-methyl-1-oxo-2-phenyl-1,2-dihydro-isoquinoline-4-carboxylic acid [(R)-cyclopropyl-(3-fluorophenyl)-methyl]-amide 1bo 8-Chloro-3-methyl-1-oxo-2-phenyl-1,2-dihydro-isoquinoline-4-carboxylic acid [cyclobutyl-(2-fluoro-phenyl)-methyl]-amide 7e 8-Fluoro-3-methyl-1-oxo-2-phenyl-1,2-dihydro-isoquinoline-4-carboxylic acid [(S)-cyclopropyl-(3-fluorophenyl)-methyl]-amide 7h 8-Fluoro-3-methyl-1-oxo-2-phenyl-1,2-dihydro-isoquinoline-4-carboxylic acid [(S)-cyclobutyl-(3-fluorophenyl)-methyl]-amide and pharmaceutically acceptable salts thereof.

Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

The compounds of the present invention may have one or more asymmetric centres and it is intended that any optical isomers (i.e. enantiomers or diastereomers), as separated, pure or partially purified optical isomers and any mixtures thereof including racemic mixtures, i.e. a mixture of stereoisomeres, are included within the scope of the invention. In particular, the carbon attached to the carboxamide N is an optical centre giving rise to two optical isomers, an R form and an S form. In one embodiment, the compounds of the present invention have the S form.

In a particular embodiment, the compounds of the present invention have the following absolute configuration around the carbon attached to the carboxamide N

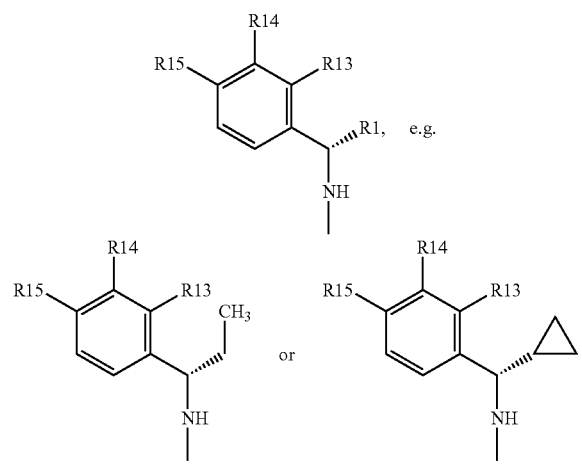

In this context is understood that when specifying the enantiomeric form, then the compound is in enantiomeric excess, e.g. essentially in a pure form. Accordingly, one embodiment of the invention relates to a compound of the invention having an enantiomeric excess of at least 60%, at least 70%, at least 80%, at least 85%, at least 90%, at least 96%, preferably at least 98%.

Racemic forms can be resolved into the optical antipodes by known methods, for example by separation of diastereomeric salts thereof with an optically active acid, and liberating the optically active amine compound by treatment with a base. Another method for resolving racemates into the optical antipodes is based upon chromatography on an optically active matrix. The compounds of the present invention may also be resolved by the formation of diastereomeric derivatives. Additional methods for the resolution of optical isomers, known to those skilled in the art, may be used. Such methods include those discussed by J. Jaques, A. Collet and S. Wilen in "Enantiomers, Racemates, and Resolutions", John Wiley and Sons, New York (1981). Optically active compounds can also be prepared from optically active starting materials.

Furthermore, molecules having a bond with restricted rotation may form geometric isomers. These are also intended to be included within the scope of the present invention.

NK3 receptor antagonists have been implicated in various diseases in addition to psychosis and schizophrenia discussed above. Langlois et al in *J. Pharm. Exp. Ther.*, 299, 712-717, 2001, concludes that NK3 antagonists may be applicable in CNS diseases in general, and in anxiety and depression in particular. Yip et al in *Br. J. Phar.*, 122, 715-722, 1997 further implicates NK3 antagonists in diverse brain functions, such as cortical processing, learning and memory, neuroendocrine and behavioral regulation. Additional studies have shown that NKB and NK3 receptors are involved in pain, and that NK3 antagonists have an antinociceptive and analgesic effect [Fioramonti, *Neurogastroenterol. Motil.*, 15, 363-369, 2003]. Mazelin et al in *Life Sci.*, 63, 293-304, 1998 show that NK3 antagonists have an effect in gut inflammation and concludes that such antagonists may be used in the treatment of irritable bowel syndrome (IBS). In addition, NK3 antagonists have in in vivo models been demonstrated to be useful in the treatment of airway related diseases, such as asthma, airway hyperresponsiveness, cough, and bronchorestriction [Daoui, *Am. J. Respir. Crit. Care Med.*, 158, 42-48, 1998]. Maubach et al in *Neurosci.*, 83, 1047-1062, 1998 show that NKB and the NK3 agonist senktide increase the frequency and duration of epileptiform discharges, and thus by inference that NK3 antagonists have a anticonvulsive potential. Finally, Kernel et al in *J. Neurosci.*, 22, 1929-1936, 2002, suggests the use of NK3 antagonists in the treatment of Parkinson's Disease.

Accordingly, clinical, pre-clinical, in vivo and in vitro studies support that NK3 receptor antagonists are of relevance for the treatment or prevention of various disorders including psychosis, schizophrenia, depression, anxiety, cognitive impairment, obesity, Alzheimer's disease, Parkinson's disease, pain, convulsions, cough, asthma, airway hyperresponsiveness, microvascular hypersensitivity, bronchoconstriction, gut inflammation, and inflammatory bowel syndrome.

Schizophrenia is classified into subgroups. The paranoid type is characterised by delusions and hallucinations and absence of thought disorder, disorganized behavior, and affective flattening. The disorganized type, which is also named 'hebephrenic schizophrenia' in the ICD, in which thought disorder and flat affect are present together. The catatonic type, in which prominent psychomotor disturbances are evident, and symptoms may include catatonic stupor and waxy flexibility. The undifferentiated type in which psychotic symptoms are present but the criteria for paranoid, disorganized, or catatonic types have not been met. The symptoms of schizophrenia normally manifest themselves in three broad categories, i.e. positive, negative and cognitive symptoms. Positive symptoms are those, which represent an "excess" of normal experiences, such as hallucinations and delusions. Negative symptoms are those where the patient suffers from a lack of normal experiences, such as anhedonia and lack of social interaction. The cognitive symptoms relate to cognitive impairment in schizophrenics, such as lack of sustained attention and deficits in decision making. The current antipsychotics are fairly successful in treating the positive symptoms but fare less well for the negative and cognitive symptoms. Contrary to that, NK3 antagonists have been shown clinically to improve on both positive and negative symptoms in schizophrenics [*Am. J. Psychiatry,* 161, 975-984, 204], and according to the above discussion they are also expected to deliver an effect on the cognitive symptoms.

Cognitive impairment include a decline in cognitive functions or cognitive domains, e.g. working memory, attention and vigilance, verbal learning and memory, visual learning and memory, reasoning and problem solving e.g. executive function, speed of processing and/or social cognition. In particular, cognitive impairment may indicate deficits in attention, disorganized thinking, slow thinking, difficulty in understanding, poor concentration, impairment of problem solving, poor memory, difficulties in expressing thoughts and/or difficulties in integrating thoughts, feelings and behaviour, or difficulties in extinction of irrelevant thoughts.

In one embodiment, the present invention relates to the compounds of the present invention for use in therapy.

In one embodiment, the present invention relates to a method of treating a disease selected from psychosis; schizophrenia; schizophreno form disorder; schizoaffective disorder; delusional disorder; brief psychotic disorder; shared psychotic disorder; psychotic disorder due to a general medical condition; substance or drug induced psychotic disorder (cocaine, alcohol, amphetamine etc); schizoid personality disorder; schizoptypal personality disorder; psychosis or schizophrenia associated with major depression, bipolar disorder, Alzheimer's disease or Parkinson's disease; major depression; general anxiety disorder; bipolar disorder (maintenance treatment, recurrence prevention and stabilization); mania; hypomania; cognitive impairment; ADHD; obesity; appetite reduction; Alzheimer's disease; Parkinson's disease; pain; convulsions; cough; asthma; airway hyperresponsiveness; microvascular hypersensitivity; bronchoconstriction; chronic obstructive pulmonary disease; urinary incontinence; gut inflammation; and inflammatory bowel syndrome the method comprising the administration of a therapeutically effective amount of a compound of the present invention to a patient in need thereof.

In one embodiment, the present invention relates to a method for the treatment of schizophrenia, the method comprising the administration of a therapeutically effective amount of a compound of the present invention to a patient in need thereof. In particular, said treatment includes the treatment of the positive, negative and/or cognitive symptoms of schizophrenia.

In one embodiment, the present invention relates to a method of treating cognitive impairment, the method comprising the administration of a therapeutically effective amount of a compound of the present invention to a patient in need thereof. In particular, said cognitive impairment is manifested as a decline in working memory, attention and vigilance, verbal learning and memory, visual learning and memory, reasoning and problem solving e.g. executive function, speed of processing and/or social cognition.

The antipsychotic effect of typical and atypical anti-psychotics, in particular D2 antagonists is exerted via an inhibition of the post-synaptic D2 receptors. Pre-synaptic D2 auto-receptors, however, are also affected by the administration of these compounds giving rise to an increase in the dopamine neuron firing rate, which, in fact, counteracts the antipsychotic effects. The increased firing rate continues until the effect of the pre-synaptic auto-receptors is blocked (the depolarization block), typically after approximately 3 weeks of chronic treatment with typical or atypical anti-psychotics. This model explains the up to 3 weeks delay of clinical effect normally seen when D2 antagonist treatment is initiated. NK3 antagonists seem to inhibit the increase in the dopamine neuron firing mediated by the pre-synaptic D2 auto-receptors brought about by D2 antagonists, wherefore the combined administration of NK3 antagonists and D2 antagonists is expected to give rise to a faster onset of the clinical effect. Moreover, D2 antagonists are known to increase prolactin levels, which may give rise to serious side effects, such as osteoporosis. It is known that NK3 agonists give rise to an increase in prolactin from which it may be deduced that a NK3 antagonist will lower an increased prolactin level, i.e. normalise the prolactin level. A combined use of NK3 antagonists and D2 antagonists may thus address some of the safety aspects associated with D2 antagonists administration. Similarly, NK3 antagonists may be administered together with antagonists/inverse agonists/negative modulators/partial agonists of one or more of the targets dopamine D2 receptor, dopamine D3 receptor, dopamine D4 receptor, phosphodiesterase PDE10, serotonin $5\text{-HT}_{1A}$ receptor, serotonin $5\text{-HT}_{2A}$ receptor, serotonin $5\text{-HT}_6$ receptor, adrenergic alpha 2 receptor, cannabinoid type 1 receptor, histamine H3 receptor, cyclooxygenases, sodium channels or glycine transporter GlyT1; or with agonists/positive modulators/partial agonists of one or more of the targets serotonin $5\text{-HT}_{2C}$ receptor, KCNQ channels, NMDA receptor, AMPA receptor, nicotinic alpha-7 receptor, muscarinic M1 receptor, muscarinic M4 receptor, metabotropic glutamate receptor mGluR2, metabotropic glutamate receptor mGluR5, dopamine D1 receptor or dopamine D5 receptor.

Such combined administration of compounds of the present invention and other anti-psychotic compounds, such as D2 antagonists, D2 partial agonists, PDE10 antagonists, $5\text{-HT}_{2A}$ antagonists, $5\text{-HT}_6$ antagonists or KCNQ4 antagonists may be sequential or concomitant. Examples of D2 antagonists or partial agonists include haloperidol, chlorpromazine, sulpirid, risperidone, ziprasidon, olanzapine, quetiapin, and clozapine.

In one embodiment, the compound of the present invention is administered in an amount from about 0.001 mg/kg body weight to about 100 mg/kg body weight per day. In particular, daily dosages may be in the range of 0.01 mg/kg body weight to about 50 mg/kg body weight per day. The exact dosages will depend upon the frequency and mode of administration, the sex, the age the weight, and the general condition of the subject to be treated, the nature and the severity of the condition to be treated, any concomitant diseases to be treated, the desired effect of the treatment and other factors known to those skilled in the art.

A typical oral dosage for adults will be in the range of 1-1000 mg/day of a compound of the present invention, such as 1-500 mg/day.

In one embodiment, the present invention relates to the use of the compounds of the present invention in the manufacture of a medicament for the treatment of a disease selected from psychosis; schizophrenia; schizophrenoform disorder; schizoaffective disorder; delusional disorder; brief psychotic disorder; shared psychotic disorder; psychotic disorder due to a general medical condition; substance or drug induced psychotic disorder (cocaine, alcohol, amphetamine etc); schizoid personality disorder; schizoptypal personality disorder; psychosis or schizophrenia associated with major depression, bipolar disorder, Alzheimer's disease or Parkinson's disease; major depression; general anxiety disorder; bipolar disorder (maintenance treatment, recurrence prevention and stabilization); mania; hypomania; cognitive impairment; ADHD; obesity; appetite reduction; Alzheimer's disease; Parkinson's disease; pain; convulsions; cough; asthma; airway hyperresponsiveness; microvascular hypersensitivity; bronchoconstriction; chronic obstructive pulmonary disease; urinary incontinence; gut inflammation; and inflammatory bowel syndrome.

In one embodiment, the present invention relates to the use of a compound of the present invention in the manufacture of a medicament for the treatment of schizophrenia. In particular, said treatment includes the treatment of the positive, negative and/or cognitive symptoms of schizophrenia.

In one embodiment, the present invention relates to the use of a compound of the present invention in the manufacture of a medicament for the treatment of cognitive impairment. In particular, said cognitive impairment is manifested as a decline in working memory, attention and vigilance, verbal learning and memory, visual learning and memory, reasoning and problem solving e.g. executive function, speed of processing and/or social cognition.

In one embodiment, the present invention relates to a compound of the present invention for use in the treatment of a disease selected from psychosis; schizophrenia; schizophreniform disorder; schizoaffective disorder; delusional disorder; brief psychotic disorder; shared psychotic disorder; psychotic disorder due to a general medical condition; substance or drug induced psychotic disorder (cocaine, alcohol, amphetamine etc); schizoid personality disorder; schizotypal personality disorder; psychosis or schizophrenia associated with major depression, bipolar disorder, Alzheimer's disease or Parkinson's disease; major depression; general anxiety disorder; bipolar disorder (maintenance treatment, recurrence prevention and stabilization); mania; hypomania; cognitive impairment; ADHD; obesity; appetite reduction; Alzheimer's disease; Parkinson's disease; pain; convulsions; cough; asthma; airway hyperresponsiveness; microvascular hypersensitivity; bronchoconstriction; chronic obstructive pulmonary disease; urinary incontinence; gut inflammation; and inflammatory bowel syndrome.

In one embodiment, the present invention relates to a compound of the present invention for use in the treatment of schizophrenia. In particular, said treatment includes the treatment of the positive, negative and/or cognitive symptoms of schizophrenia.

In one embodiment, the present invention relates to a compound of the present invention for use in the treatment of cognitive impairment. In particular, said cognitive impairment is manifested as a decline in working memory, attention and vigilance, verbal learning and memory, visual learning and memory, reasoning and problem solving e.g. executive function, speed of processing and/or social cognition.

The compounds of the present invention may be administered alone as a pure compound or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19 Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the actually chosen route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings.

Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use.

Other suitable administration forms include suppositories, sprays, ointments, cremes, gels, inhalants, dermal patches, implants, etc.

Conveniently, the compounds of the invention are administered in a unit dosage form containing said compounds in an amount of about 0.1 to 500 mg, such as 10 mg, 50 mg 100 mg, 150 mg, 200 mg or 250 mg of a compound of the present invention.

For parenteral routes such as intravenous, intrathecal, intramuscular and similar administration, typically doses are in the order of about half the dose employed for oral administration.

For parenteral administration, solutions of the compound of the invention in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospho lipids, fatty acids, fatty acid amines, polyoxyethylene and water. The pharmaceutical compositions formed by combining the compound of the invention and the pharmaceutical acceptable carriers are then readily administered in a variety of dosage forms suitable for the disclosed routes of administration.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tablet, e.g. placed in a hard gelatine capsule in powder or pellet form or in the form of a troche or lozenge. The amount of solid carrier may vary but will usually be from about 25 mg to about 1 g.

If a liquid carrier is used, the preparation may be in the form of a syrup, emulsion, soft gelatine capsule or sterile injectable liquid such as an aqueous or non-aqueous liquid suspension or solution.

Tablets may be prepared by mixing the active ingredient with ordinary adjuvants and/or diluents followed by the compression of the mixture in a conventional tabletting machine. Examples of adjuvants or diluents comprise: Corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

In one embodiment, the invention relates to a pharmaceutical composition comprising a compound of the present invention together with a second anti-psychotic agent. In one embodiment, said second anti-psychotic agent is selected from antagonists/inverse agonists/negative modulators/partial agonists of the targets dopamine D2 receptor, dopamine D3 receptor, dopamine D4 receptor, phosphodiesterase PDE10, serotonin 5-HT$_{1A}$ receptor, serotonin 5-HT$_{2A}$ receptor, serotonin 5-HT$_6$ receptor, adrenergic alpha 2 receptor, cannabinoid type 1 receptor, histamine H3 receptor, cyclooxygenases, sodium channels or glycine transporter GlyT1; or from agonists/positive modulators/partial agonists of the targets serotonin 5-HT$_{2C}$ receptor, KCNQ channels, NMDA receptor, AMPA receptor, nicotinic alpha-7 receptor, muscarinic M1 receptor, muscarinic M4 receptor, metabotropic glutamate receptor mGluR2, metabotropic glutamate receptor mGluR5, dopamine D1 receptor or dopamine D5 receptor. In one embodiment, said second anti-psychotic agent is selected from typical anti-psychotics, atypical anti-psychotics, D2 antagonists, partial D2 agonists, PDE10 antagonists, 5-HT$_{2A}$ antagonists, 5-HT$_6$ antagonists and KCNQ4 antagonists, and in particular atypical anti-psychotics, D2 antagonists, partial D2 agonists. Particular examples of such anti-psychotics include haloperidol, chlorpromazine, sulpirid, risperidone, ziprasidon, olanzapine, quetiapine, and clozapine.

In one embodiment, the invention relates to a pharmaceutical kit comprising a container comprising a compound of the present invention and a separate container comprising an anti-psychotic drug. Typical anti-psychotics, atypical anti-psychotics, D2 antagonists, partial D2 agonists, PDE10 antagonists, 5-HT$_{2A}$ antagonists, 5-HT$_6$ antagonists and KCNQ4 antagonists, and in particular atypical anti-psychotics, D2 antagonists, partial D2 agonists. Particular examples of such anti-psychotics include haloperidol, chlorpromazine, sulpirid, risperidone, ziprasidon, olanzapine, quetiapine, and clozapine.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various "compounds" of the invention or particular described aspect, unless otherwise indicated.

Unless otherwise indicated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

Synthetic Routes

Compounds according to the present invention can be prepared as described in WO 2008/131779. For convenience, the number indicated in bold in front of the exemplified compound name refers to the corresponding example number in WO2008/131779.

Example 1

NK3 Receptor Efficacy and Potency Assay

BHK cells stably expressing the human NK3 receptor were seeded in 100 µl media in black walled clear-base 96-wells plates (Costar) aiming at a confluency of 95-100% at the day of assay. The assay was performed according to the FLIPR Calcium 4 Assay kit (Molecular Devices). At the day of the assay, the media was removed and the cells were washed once with the HBSS buffer (Hanks BSS buffer, pH 7.4 containing 20 mM Hepes) before 100 µl of a solution of the calcium assay reagent dissolved in the HBSS buffer containing 2.5 mM probinicid was added to the cells. The plates were incubated for 60 min at 34° C., 10% $CO_2$ before use in the FLIPR for examination of fluorescence.

One representative plate was examined with a dose-response curve with NKB in a setup in which the wells initially were added HBSS buffer and 15 min later the various concentrations of NKB were added in order to determine the $EC_{50}$ and $EC_{85}$ of NKB. All compound plates used for NKB were precoated with a 1% BSA solution and subsequently washed three times with $H_2O$, NKB was diluted in HBSS buffer containing 0.1% BSA.

For efficacy and potency evaluation of compounds, these were diluted in HBSS buffer prior to test. For test of agonist activity, 25 µl of the diluted compound solution was added and the plate was analyzed for 5 minutes in the FLIPR. For test of antagonist activity, the plate was incubated for another 45 minutes before addition of 25 µl of the $EC_{85}$ concentration of NKB (app. 2 nM) as described above. The plates were subsequently analyzed for 5 minutes before the assay was terminated. The maximal increase in fluorescence over background following each ligand addition was determined. The $IC_{50}$ value was calculated using sigmoidal variable slope curve fitting, and the $cIC_{50}$ value was determined using the equation ($cIC_{50}=IC_{50}/(1+(EC_{85}/EC_{50}))$), where $EC_{85}$ and $EC_{50}$ for NKB were determined as described above.

All isoquinolinones of the present invention characterized in the NK3 receptor efficacy and potency assay have been antagonists without any observed significant agonist activity at relevant doses. The compounds of the present invention generally have $K_i$ values below 500 nM. Many compounds, in fact have $K_i$ values well below 100 nM. The table shows affinity data and potency data obtained with the compounds of the invention.

| Example No | Affinity $K_i$/nM | Potency $cIC_{50}$/nM |
| --- | --- | --- |
| 1as | 250 | 240 |
| 1at | 180 | 150 |
| 1au | 270 | 260 |
| 1av | 39 | 110 |
| 1aw | 59 | 130 |
| 1ax | 150 | 170 |
| 1ay | 47 | 100 |
| 1ba | 55 | 150 |
| 1bb | 240 | 350 |
| 1bd | 49 | 87 |
| 1be | 45 | 100 |
| 1bh | 31 | 43 |
| 1bi | 31 | 47 |
| 1bl | 810 | 620 |
| 1bo | 150 | 92 |
| 7e | 15 | 21 |
| 7h | 10 | 22 |

The invention claimed is:

1. A compound according to formula Ik"

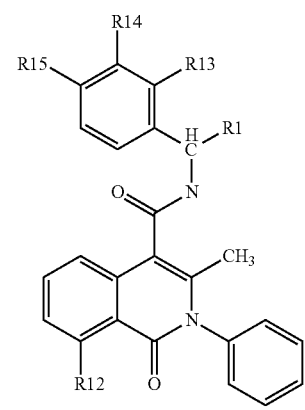

[Ik"]

wherein $R^1$ represents ethyl, cyclopropyl or cyclobutyl;

wherein $R^{12}$ represents fluoro or chloro; and $R^{13}$, $R^{14}$ and $R^{15}$ each individually represent hydrogen, fluoro or chloro, wherein two of $R^{13}$, $R^{14}$ and $R^{15}$ represent hydrogen;

or a pharmaceutically acceptable salt thereof.

2. The compound according to claim 1, wherein said compound is essentially the S enantiomers as depicted in formula Ik'"

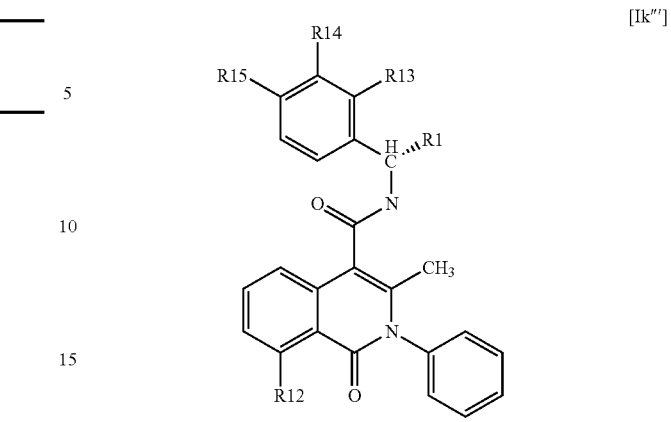

[Ik'"]

wherein $R^1$ represents ethyl or cyclopropyl;

wherein $R^{12}$ represents fluoro or chloro; and $R^{13}$, $R^{14}$ and $R^{15}$ each individually represent hydrogen, fluoro or chloro, wherein two of $R^{13}$, $R^{14}$ and $R^{15}$ represent hydrogen;

or a pharmaceutically acceptable salt thereof.

3. A compound selected from the group consisting of:

8-Chloro-3-methyl-1-oxo-2-phenyl-1,2-dihydro-isoquinoline-4-carboxylic acid [(S)-1-(4-chloro-phenyl)-propyl]-amide;

8-Chloro-3-methyl-1-oxo-2-phenyl-1,2-dihydro-isoquinoline-4-carboxylic acid [(S)-1-(4-fluoro-phenyl)-propyl]-amide;

8-Chloro-3-methyl-1-oxo-2-phenyl-1,2-dihydro-isoquinoline-4-carboxylic acid [(S)-1-(2-fluoro-phenyl)-propyl]-amide;

8-Chloro-3-methyl-1-oxo-2-phenyl-1,2-dihydro-isoquinoline-4-carboxylic acid [(S)-1-(3-chloro-phenyl)-propyl]-amide;

8-Chloro-3-methyl-1-oxo-2-phenyl-1,2-dihydro-isoquinoline-4-carboxylic acid [(S)-(3-chloro-phenyl)-cyclopropyl-methyl]-amide;

8-Chloro-3-methyl-1-oxo-2-phenyl-1,2-dihydro-isoquinoline-4-carboxylic acid [(S)-(4-chloro-phenyl)-cyclopropyl-methyl]-amide;

8-Chloro-3-methyl-1-oxo-2-phenyl-1,2-dihydro-isoquinoline-4-carboxylic acid [(S)-1-(3-fluoro-phenyl)-propyl]-amide;

8-Chloro-3-methyl-1-oxo-2-phenyl-1,2-dihydro-isoquinolone-4-carboxylic acid [(S)-cyclopropyl-(4-fluoro-phenyl)-methyl]-amide;

8-Chloro-3-methyl-1-oxo-2-phenyl-1,2-dihydro-isoquinoline-4-carboxylic acid [(S)-1-(2-chloro-phenyl)-propyl]-amide;

8-Chloro-3-methyl-1-oxo-2-phenyl-1,2-dihydro-isoquinoline-4-carboxylic acid [(S)-(2-chloro-phenyl)-cyclopropyl-methyl]-amide;

8-Chloro-3-methyl-1-oxo-2-phenyl-1,2-dihydro-isoquinoline-4-carboxylic acid [(S)-cyclopropyl-(2-fluoro-phenyl)-methyl]-amide;

8-Chloro-3-methyl-1-oxo-2-phenyl-1,2-dihydro-isoquinoline-4-carboxylic acid [(S)-cyclobutyl-(3-fluoro-phenyl)-methyl]-amide;

8-Chloro-3-methyl-1-oxo-2-phenyl-1,2-dihydro-isoquinoline-4-carboxylic acid [(S)-cyclobutyl-(4-fluoro-phenyl)-methyl]-amide;

8-Chloro-3-methyl-1-oxo-2-phenyl-1,2-dihydro-isoquinoline-4-carboxylic acid [(R)-cyclopropyl-(3-fluoro-phenyl)-methyl]-amide;

8-Chloro-3-methyl-1-oxo-2-phenyl-1,2-dihydro-isoquinoline-4-carboxylic acid [cyclobutyl-(2-fluoro-phenyl)-methyl]-amide;

8-Fluoro-3-methyl-1-oxo-2-phenyl-1,2-dihydro-isoquinoline-4-carboxylic acid [(S)-cyclopropyl-(3-fluoro-phenyl)-methyl]-amide; and 8-Fluoro-3-methyl-1-oxo-2-phenyl-1,2-dihydro-isoquinoline-4-carboxylic acid [(S)-cyclobutyl-(3-fluoro-phenyl)-methyl]-amide;

or a pharmaceutically acceptable salt thereof.

4. The compound according to claim 3, wherein the compound is selected from the group consisting of:

8-Chloro-3-methyl-1-oxo-2-phenyl-1,2-dihydro-isoquinoline-4-carboxylic acid [(S)-1-(4-chloro-phenyl)-propyl]-amide;

8-Chloro-3-methyl-1-oxo-2-phenyl-1,2-dihydro-isoquinoline-4-carboxylic acid [(S)-1-(4-fluoro-phenyl)-propyl]-amide;

8-Chloro-3-methyl-1-oxo-2-phenyl-1,2-dihydro-isoquinoline-4-carboxylic acid [(S)-1-(2-fluoro-phenyl)-propyl]-amide;

8-Chloro-3-methyl-1-oxo-2-phenyl-1,2-dihydro-isoquinoline-4-carboxylic acid [(S)-1-(3-chloro-phenyl)-propyl]-amide; and 8-Chloro-3-methyl-1-oxo-2-phenyl-1,2-dihydro-isoquinoline-4-carboxylic acid [(S)-(3-chloro-phenyl)-cyclopropyl-methyl]-amide;

or a pharmaceutically acceptable salt thereof.

5. The compound according to claim 3 wherein the compound is selected from the group consisting of:

8-Chloro-3-methyl-1-oxo-2-phenyl-1,2-dihydro-isoquinoline-4-carboxylic acid [(S)-(4-chloro-phenyl)-cyclopropyl-methyl]-amide;

8-Chloro-3-methyl-1-oxo-2-phenyl-1,2-dihydro-isoquinoline-4-carboxylic acid [(S)-1-(3-fluoro-phenyl)-propyl]-amide;

8-Chloro-3-methyl-1-oxo-2-phenyl-1,2-dihydro-isoquinoline-4-carboxylic acid [(S)-cyclopropyl-(4-fluoro-phenyl)-methyl]-amide;

8-Chloro-3-methyl-1-oxo-2-phenyl-1,2-dihydro-isoquinoline-4-carboxylic acid [(S)-1-(2-chloro-phenyl)-propyl]-amide; and 8-Chloro-3-methyl-1-oxo-2-phenyl-1,2-dihydro-isoquinoline-4-carboxylic acid [(S)-(2-chloro-phenyl)-cyclopropyl-methyl]-amide;

or a pharmaceutically acceptable salt thereof.

6. The compound according to claim 3, wherein the compound is selected from the group consisting of:

8-Chloro-3-methyl-1-oxo-2-phenyl-1,2-dihydro-isoquinoline-4-carboxylic acid [(S)-cyclopropyl-(2-fluoro-phenyl)-methyl]-amide;

8-Chloro-3-methyl-1-oxo-2-phenyl-1,2-dihydro-isoquinoline-4-carboxylic acid [(S)-cyclobutyl-(3-fluoro-phenyl)-methyl]-amide;

8-Chloro-3-methyl-1-oxo-2-phenyl-1,2-dihydro-isoquinoline-4-carboxylic acid [(S)-cyclobutyl-(4-fluoro-phenyl)-methyl]-amide;

8-Chloro-3-methyl-1-oxo-2-phenyl-1,2-dihydro-isoquinoline-4-carboxylic acid [(R)-cyclopropyl-(3-fluoro-phenyl)-methyl]-amide; and 8-Chloro-3-methyl-1-oxo-2-phenyl-1,2-dihydro-isoquinoline-4-carboxylic acid [cyclobutyl-(2-fluoro-phenyl)-methyl]-amide;

or a pharmaceutically acceptable salt thereof.

7. The compound according to claim 3, wherein the compound is

8-Fluoro-3-methyl-1-oxo-2-phenyl-1,2-dihydro-isoquinoline-4-carboxylic acid [(S)-cyclopropyl-(3-fluoro-phenyl)-methyl]-amide; or 8-Fluoro-3-methyl-1-oxo-2-phenyl-1,2-dihydro-isoquinoline-4-carboxylic acid [(S)-cyclobutyl-(3-fluoro-phenyl)-methyl]-amide;

or a pharmaceutically acceptable salt thereof.

8. A method for the treatment of a disease selected from psychosis; schizophrenia; schizophrenoform disorder; schizoaffective disorder; delusional disorder; brief psychotic disorder; shared psychotic disorder; psychotic disorder due to a general medical condition; substance or drug induced psychotic disorder; schizoid personality disorder; schizoptypal personality disorder; psychosis or schizophrenia associated with major depression, bipolar disorder, Alzheimer's disease or Parkinson's disease; major depression; general anxiety disorder; bipolar disorder; mania; hypomania; cognitive impairment; ADHD; obesity; appetite reduction; Alzheimer's disease; Parkinson's disease; pain; convulsions; cough; asthma; airway hyperresponsiveness; microvascular hypersensitivity; bronchoconstriction; chronic obstructive pulmonary disease; urinary incontinence; gut inflammation; and inflammatory bowel syndrome, which method comprises the administration of a therapeutically effective amount of a compound according to claim 1 to a patient in need thereof.

9. The method according to claim 8, wherein said disease is schizophrenia.

10. The method according to claim 9, wherein said treatment comprises the treatment of positive, negative and/or cognitive symptoms of schizophrenia.

11. The method according to claim 9 which comprises a concomitant or sequential administration of a therapeutically effective amount of a compound selected from the list consisting of D2 antagonists, D2 partial agonists, PDE10 antagonists, $5\text{-}HT_{2A}$ antagonists, $5\text{-}HT_6$ antagonists and KCNQ4 antagonists.

12. A pharmaceutical composition comprising a compound according to claim 1 and one or more pharmaceutically acceptable carriers or excipients.

13. The composition according to claim 12 which composition comprises a compound selected from the list consisting of D2 antagonists, D2 partial agonists, PDE10 antagonists, $5\text{-}HT_{2A}$ antagonists, $5\text{-}HT_6$ antagonists and KCNQ4 antagonists.

14. A kit comprising a compound according to claim 1 together with a compound selected from the list consisting of D2 antagonists, D2 partial agonists, PDE10 antagonists, $5\text{-}HT_{2A}$ antagonists, $5\text{-}HT_6$ antagonists and KCNQ4 antagonists.

* * * * *

UNITED STATES PATENT AND TRADEMARK OFFICE
CERTIFICATE OF CORRECTION

PATENT NO. : 8,420,667 B2
APPLICATION NO. : 12/988631
DATED : April 16, 2013
INVENTOR(S) : Khanzhin et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 241 days.

Signed and Sealed this
Thirtieth Day of December, 2014

Michelle K. Lee
*Deputy Director of the United States Patent and Trademark Office*